United States Patent
Fukatsu et al.

(10) Patent No.: US 11,938,464 B2
(45) Date of Patent: Mar. 26, 2024

(54) ANALYTICAL METHOD FOR SUGAR CHAINS HAVING ACIDIC GROUPS

(71) Applicant: JCR Pharmaceuticals Co., Ltd., Ashiya (JP)

(72) Inventors: Tomoki Fukatsu, Kobe (JP); Chika Morooka, Kobe (JP)

(73) Assignee: JCR Pharmaceuticals Co., Ltd., Ashiya (JP)

( * ) Notice: Subject to any disclaimer, the term of this patent is extended or adjusted under 35 U.S.C. 154(b) by 0 days.

(21) Appl. No.: 18/147,894

(22) Filed: Dec. 29, 2022

(65) Prior Publication Data
US 2023/0219063 A1 Jul. 13, 2023

Related U.S. Application Data

(62) Division of application No. 16/763,285, filed as application No. PCT/JP2018/042064 on Nov. 14, 2018, now abandoned.

(30) Foreign Application Priority Data

Nov. 15, 2017 (JP) .................................. 2017-219669

(51) Int. Cl.
*B01D 15/18* (2006.01)
*B01D 15/30* (2006.01)
(Continued)

(52) U.S. Cl.
CPC ........ *B01J 20/283* (2013.01); *B01D 15/1871* (2013.01); *B01D 15/305* (2013.01);
(Continued)

(58) Field of Classification Search
CPC .... B01J 20/283; B01J 20/285; B01J 20/3219; B01J 20/3248; B01J 20/286; B01J 41/05;
(Continued)

(56) References Cited

U.S. PATENT DOCUMENTS

| 2015/0087816 A1 | 3/2015 | Forrer et al. |
| 2015/0204824 A1 | 7/2015 | Lauber et al. |

(Continued)

FOREIGN PATENT DOCUMENTS

| EP | 0 353 015 A2 | 1/1990 |
| EP | 2 745 904 A1 | 6/2014 |

(Continued)

OTHER PUBLICATIONS

Machine translation of JP 2016-530535-A.*

(Continued)

*Primary Examiner* — Benjamin L Lebron
(74) *Attorney, Agent, or Firm* — Oblon, McClelland, Maier & Neustadt, L.L.P.

(57) ABSTRACT

A chromatography column for the use of separation of acidic sugar chains, wherein the column comprises a first column and a second column, the second column connected by a flow path downstream of an outlet of the first column, and selected from the following (1) or (2): (1) the carrier of the first column is hydrophobically modified silica having a group containing a primary amine, a secondary amine or/and a tertiary amine, and the carrier of the second column is a resin having a group containing a primary amine, a secondary amine or/and a tertiary amine; (2) the carrier of the first column is a resin having a group containing a primary amine, a secondary amine or/and a tertiary amine, and the carrier of the second column is hydrophobically modified silica having a group containing a primary amine, a secondary amine, or/and a tertiary amine.

7 Claims, 2 Drawing Sheets
Specification includes a Sequence Listing.

(51) Int. Cl.

| | |
|---|---|
| *B01D 15/36* | (2006.01) |
| *B01J 20/283* | (2006.01) |
| *B01J 20/285* | (2006.01) |
| *B01J 20/286* | (2006.01) |
| *B01J 20/32* | (2006.01) |
| *B01J 41/05* | (2017.01) |
| *B01J 41/07* | (2017.01) |
| *B01J 41/14* | (2006.01) |
| *B01J 41/20* | (2006.01) |
| *C07K 16/00* | (2006.01) |
| *G01N 30/06* | (2006.01) |
| *G01N 30/34* | (2006.01) |
| *G01N 30/46* | (2006.01) |
| *G01N 30/74* | (2006.01) |
| *G01N 30/88* | (2006.01) |

(52) U.S. Cl.
CPC .......... *B01D 15/363* (2013.01); *B01J 20/285* (2013.01); *B01J 20/286* (2013.01); *B01J 20/3219* (2013.01); *B01J 20/3248* (2013.01); *B01J 41/05* (2017.01); *B01J 41/07* (2017.01); *B01J 41/14* (2013.01); *B01J 41/20* (2013.01); *G01N 30/06* (2013.01); *G01N 30/34* (2013.01); *G01N 30/46* (2013.01); *G01N 30/461* (2013.01); *G01N 30/74* (2013.01); *G01N 30/88* (2013.01); *C07K 16/00* (2013.01); *G01N 2030/067* (2013.01); *G01N 2030/8836* (2013.01)

(58) Field of Classification Search
CPC . B01J 41/07; B01J 41/14; B01J 41/20; G01N 30/06; G01N 30/46; G01N 30/74; G01N 30/88; G01N 30/34; G01N 30/461; G01N 2030/067; G01N 2030/8836; B01D 15/1871; B01D 15/305; B01D 15/363; C07K 16/00
See application file for complete search history.

(56) References Cited

U.S. PATENT DOCUMENTS

| | | |
|---|---|---|
| 2015/0316515 A1 | 11/2015 | Lauber et al. |
| 2016/0024141 A1 | 1/2016 | Issa et al. |
| 2017/0007981 A1 | 1/2017 | Nakajima |

FOREIGN PATENT DOCUMENTS

| | | | |
|---|---|---|---|
| JP | 8-228795 A | | 9/1996 |
| JP | 9-127090 A | | 5/1997 |
| JP | 2005-91953 A | | 4/2005 |
| JP | 2005-241389 A | | 9/2005 |
| JP | 2008-309699 A | | 12/2008 |
| JP | 2015-91953 A | | 5/2015 |
| JP | 2016530535 A | * | 9/2016 |

OTHER PUBLICATIONS

Togawa, T., et al., "Comparative study on mannose 6-phosphate residue contents of recombinant lysosomal enzymes", Molecular Genetics and Metabolism, 111, pp. 369-373. (Year: 2014).*
International Search Report dated Feb. 19, 2019 in PCT/JP2018/042064 filed on Nov. 14, 2018, 2 pages.
Kuraya et. al., "Release of O-Linked Sugar Chains from Glycoproteins with Anhydrous Hydrazine and Pyridylamination of the Sugar Chains with Improved Reaction Conditions," *J. Biochem.* vol. 112, No. 1, pp. 122-126, 1992 (total 5 pages).
Kondo et. al., "Improved Method for Flourescence Labeling of Sugar Chains with Sialic Acid Residues," *Agric Biol. Chem.*, vol. 54, No. 8, pp. 2169-2170, 1990 (total 2 pages).
Deguchi et al., "Two-dimensional hydrophilic interaction chromatography coupling anion-exchange and hydrophilic interaction columns for separation of 2-pyridylamino derivatives of neutral and sialylated N-glycans," Elsevier, ScienceDirect, Journal of Chromatography A, vol. 1189, pp. 169-174, 2008, doi:10.1016/j.chroma.2007.09.028 (total 6 pages).
Nakagawa, "Carbohydrate structure analysis by $2/3$-dimensional mapping," Clinical chemistry vol. 34, No. 4, pp. 319-325, 2005 (with unedited computer generated English translation) (total 20 pages).
Kondo et al., "Separation of Pyridylamino Oligosaccharides by High-Performance Liquid Chromatography on an Amine-Bearing Silica Column," Analytical Biochemistry, vol. 219, pp. 21-25, 1994 (total 5 pages).
Ikegami et al., "A Perspective of Hydrophilic Interaction Chromatography-Development and the Characteristics of the separation mode," Chromatography, vol. 29, No. 2, pp. 1-6, 2008 (with English abstract) (total 6 pages).
Millipore Sigma, "TSKgel(R) DEAE-5PW HPLC Column", Merck KGaA, 2021.
Millipore Sigma, "TSKgel(R) Amide-80 HPLC Column", Merck KGaA, 2021.
Olsen, B., "Hydrophilic interaction chromatography using amino and silica columns for the determination of polar pharmaceuticals and impurities", Journal of Chromatography A, 913, pp. 113-122. (Year: 2001)
Peng, Y., et al., "A hyperbranched polyethyleneimine functionalized stationary phase for hydrophilic interaction liquid chromatography", Anal Bioanal Chem 408, pp. 3633-3638. (Year: 2016).
Shodex, "Asahipak N H2P". Jun. 2016.
Mendez, A., et al., "Comparison of the acidity of residual silanol groups in several liquid chromatography columns", Journal of Chromatography A, 986, pp. 33-44. (Year: 2003).

* cited by examiner

ANALYTICAL METHOD FOR SUGAR CHAINS HAVING ACIDIC GROUPS

CROSS-REFERENCE TO RELATED APPLICATIONS

The present application is a divisional of U.S. application Ser. No. 16/763,285, filed May 12, 2020, which is a 35 U.S.C. § 371 national stage patent application of International patent application PCT/JP2018/042064, filed on Nov. 14, 2018, which is based on and claims the benefits of priority to Japanese Application No. 2017-219669, filed on Nov. 15, 2017. The entire contents of all of the above applications are incorporated herein by reference.

REFERENCE TO A SEQUENCE LISTING

In accordance with 37 CFR § 1.52(e)(5), the present specification makes reference to a Sequence Listing submitted electronically as a .xml file named "545931US_ST26". The .xml file was generated on Dec. 23, 2022 and is 16,959 bytes in size. The entire contents of the Sequence Listing are hereby incorporated by reference.

TECHNICAL FIELD

The present invention relates to a method for separating and analyzing acidic sugar chains having acidic groups, and more particularly, to a chromatography column which can be used for separating acidic sugar chains, and to a method for separating and analyzing sugar chains having acidic groups contained in glycoproteins using the chromatography column.

BACKGROUND OF THE INVENTION

As a method for analyzing the sugar chain structure of a glycoprotein, a method has been known in which a glycoprotein is trypsinized and treated with glycosidase to liberate sugar chains from the glycoprotein, and then this sugar chain is labeled with 2-aminopyridine (2-aminopyridine label), and subjected to normal phase column chromatography for separation analysis (Non-Patent Document 1).

The 2-aminopyridine labeling of a sugar chain is performed, for example, by adding a 2-aminopyridine solution to a sample containing a sugar chain and performing a heating reaction to form an imine, followed by adding a borane-dimethylamine complex solution and heating to reduce the imine (Non-Patent Document 1).

Next, in order to remove unreacted 2-aminopyridine and the like, a 1:1 mixture of triethylamine and methanol, and toluene to the reacted solution, and the reacted solution is dried to obtain a dried product. And this dried product is dissolved in methanol and toluene, dried again, and then dissolved in an aqueous solvent. This solution is subjected to gel filtration column chromatography to separate a sugar chain labeled with 2-aminopyridine.

As described above, the method of labeling the sugar chain with 2-aminopyridine includes a step of evaporation for removing an organic solvent such as toluene which is harmful to the human body (Patent Document 1 and Non-Patent Document 2).

Thus, a special device (Takara PALSTATIO Nmodel 4000, Takara Bio Inc.) for the use to label sugar chains with 2-aminopyridines had been commercially provided.

As a method for analyzing the N-linked sugar chain and the O-linked sugar chain constituting the glycoprotein, a method has been known in which the sugar chain is separated by enzymatically treating the glycoprotein, labeled with aminopyridine, and then separated by normal phase chromatography (Patent Document 2). According to this method, little organic solvent is vaporized in the course of analysis.

PRIOR ART DOCUMENTS

Patent Documents

[Patent Document 1] JP 2005-241389
[Patent Document 2] JP 2005-91953

Non-Patent Documents

[Non-Patent Document 1] Kuraya N. et. al., J. Biochem. 112. 122-6 (1992)
[Non-Patent Document 2] Kondo A. et. al., Agric. Biol. Chem. 54. 2169-70 (1990)

SUMMARY OF INVENTION

Technical Problem

An objective of the present invention is to provide a chromatography column for separating and analyzing acidic sugar chains having acidic groups such as phosphate groups and constituting glycoproteins, and a method for separating and analyzing acidic sugar chains using such a column.

Technical Solution

In research directed towards the above object, the present inventors have found that acidic sugar chains constituting glycoproteins can be separated and analyzed sensitively by using, in one embodiment, a column for hydrophilic interaction chromatography (a column for normal phase column chromatography) in which silica having a surface modified to be hydrophobic and into the surface an amino alkyl group is introduced as a functional group is used as a carrier, and a column for hydrophilic interaction chromatography (column for normal phase column chromatography) in which polyvinyl alcohol is used as a base and a resin into which an amino group is introduced as a functional group is used as a carrier, thereby completing the present invention.

Thus the present invention includes the following:
1. A chromatography column for the use of separating acidic sugar chains, wherein the column comprises a first column and a second column, the second column connected by a flow path downstream of an outlet of the first column, and selected from the following (1) or (2):
   (1) the carrier of the first column is hydrophobically modified silica having a group containing a primary amine, a secondary amine or/and a tertiary amine (carrier 1), and the carrier of the second column is a resin having a group containing a primary amine, a secondary amine or/and a tertiary amine (carrier 2);
   (2) the carrier of the first column is a resin having a group containing a primary amine, a secondary amine or/and a tertiary amine (carrier 2), and the carrier of the second column is hydrophobically modified silica having a group containing a primary amine, a secondary amine, or/and a tertiary amine (carrier 1).
2. The column of 1 above, wherein the first column and the second column both have a property as a hydrophilic interaction chromatography column.

3. The column of 1 or 2 above, wherein the carrier 2 has a property as an anion exchange resin.
4. The column of any one of 1 to 3 above, wherein the carrier 1 has a hydrophobic group represented by formula [I] and an amino group represented by formula [II]:

[Chem. 1]

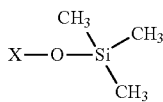
[I]

[In the formula, X represents a silica portion constituting the carrier 1]

[Chem. 2]

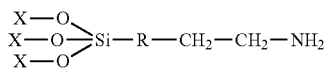
[II]

[In the formula, X represents the silica portion constituting the carrier 1, and R represents an alkyl of $-(CH_2)n-$ (n=1-8).]

5. The column of any one of 1 to 4 above, wherein the carrier 2 has an amino group represented by the general formula [III].

[Chem. 3]

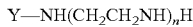
[III]

$Y-NH(CH_2CH_2NH)_nH$

[In the formula, Y represents the resin portion constituting the carrier 2, and n represents an integer of 1 to 8.]

6. The column of any one of 1 to 5 above, wherein the resin is based on polyvinyl alcohol.
7. A method for separating acidic sugar chains, the method includes:
   a step of labeling the acidic sugar chain with an aminopyridine;
   a step of loading the aminopyridine-labeled acidic sugar chain with column chromatography using the column according any one of 1-6 above, continuously directing an effluent from the column to a flow path, and continuously measuring the fluorescence intensity of the effluent flowing in the flow path,
   wherein the column chromatography is performed by passing a mobile phase through the column while successively changing the mobile phase from a first mobile phase of high hydrophobicity to a second mobile phase of low hydrophobicity, and
   a step of identifying a peak of fluorescence intensity corresponding to the acidic sugar chain in the chromatogram obtained by the measurement.
8. The method of 7 above, wherein the acidic sugar chain is that excised from a glycoprotein.
9. The method of 8 above, wherein the glycoprotein is a lysosomal enzyme.

Effect of Invention

According to the present invention, an acidic sugar chain, for example an acidic sugar chain excised from a glycoprotein by an enzyme, can be analyzed with high sensitivity.

DESCRIPTION OF EMBODIMENTS

Figure 1:
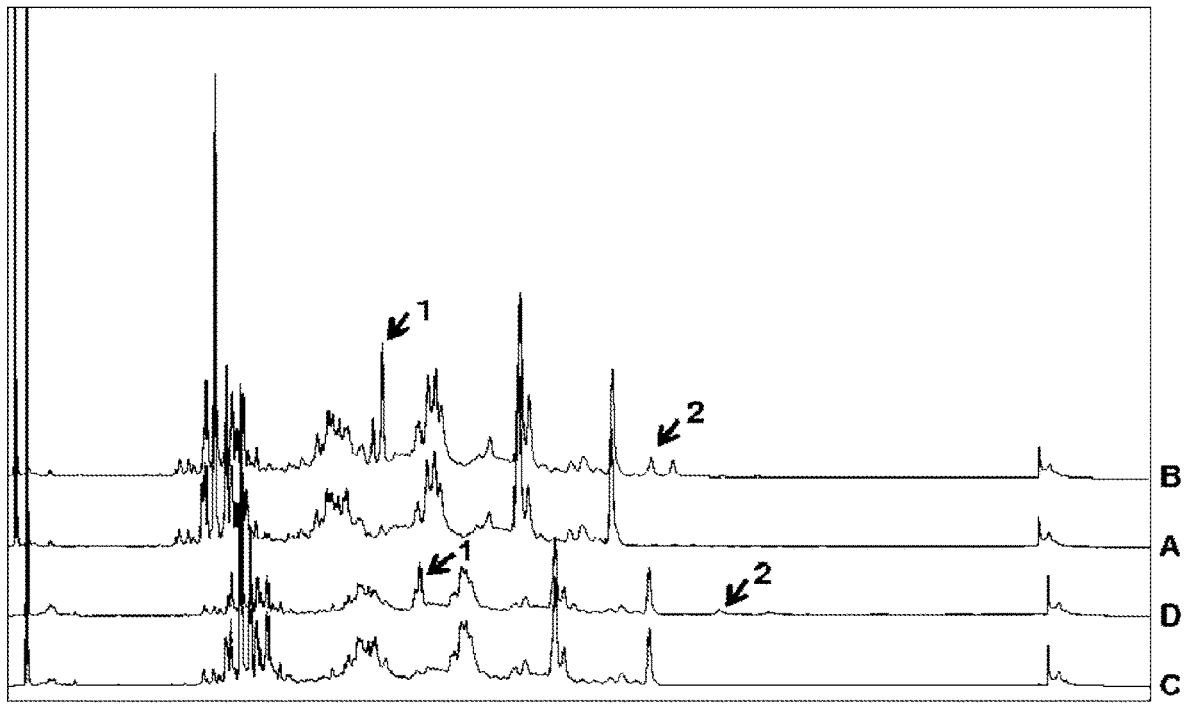
FIG. 1 shows the results of analysis of acidic sugar chains using the sugar chain profiling mobile phase B adjusted to pH 2.5. In the figure, "A" represents a chromatogram obtained by analyzing a BAP-treated sample under column chromatography condition 1 (chromatography condition 1), represents a chromatogram obtained by analyzing a BAP-untreated sample under chromatography condition 1, "C" represents a chromatogram obtained by analyzing a BAP-treated sample under column chromatography condition 2 (chromatography condition 2), and "D" represents a chromatogram obtained by analyzing a BAP-untreated sample under chromatography condition 2, respectively. Arrows 1 and 2 indicate peaks corresponding to phosphorylated sugar chains. The vertical axis represents the fluorescence intensity (400 nm) and the horizontal axis represents the retention time, respectively.

In the present invention, the term "acidic sugar chains" refers to sugar chains having acid groups such as sulfate groups, carboxyl groups, phosphate groups, and the like, including chondroitin 4-sulfate, chondroitin 6-sulfate, heparan sulfate, dermatan sulfate, keratan sulfate, and the like. Acidic sugar chains may also be included in the sugar chains that constitute the glycoprotein, and the glycoprotein has an important function in order for the glycoprotein to exert its function in the body. For example, an acidic sugar chain containing mannose-6-phosphate (M6P) at the reducing end of the sugar chain is essential for the uptake of the glycoprotein into the cell via the M6P receptor. Glycoproteins to be uptaken into cells via receptors include, for example, lysosomal enzymes such as iduronate-2-sulfatase and α-galactosidase A.

The carrier of the column used as the carrier 1 in one embodiment of the present invention is a silica modified to be hydrophobic by introducing a hydrophobic group into the surface and having a group containing a primary amine, a secondary amine, or a tertiary amine. The hydrophobic group introduced to modify the silica to be hydrophobic is not particularly limited, but is preferably an alkyl group such as a methyl group, an ethyl group, or a propyl group, and is particularly preferably a methyl group.

Such a hydrophobic group may be directly covalently bonded to a silicon atom constituting silica, or may be covalently bonded to a silicon atom via an oxygen atom. The following general formula [I] is a suitable example of a silica modified with a hydrophobic group, in which three methyl groups are bonded to a silicon atom constituting the silica. In the following general formula [I], X represents a silica portion constituting the carrier 1.

[Chem. 1]

[I]

Further, a primary amine, a secondary amine, or/and a tertiary amine contained in a silica, which is a carrier of the column used as the carrier 1, may be directly covalently bonded to a silicon atom constituting silica, or may be covalently bonded to a silicon atom via an oxygen atom. The following general formula [II] is a suitable example of a silica modified with a primary amine.

[Chem. 2]

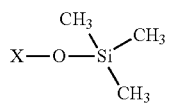

[II]

In the above general formula [II], R is an alkyl represented by $-(CH_2)_n-$ and its chain length is not particularly limited, but preferably n=1 to 10, more preferably 1 to 8, even more preferably 1 to 4, still more preferably 1 to 3, for example, n=1, n=2, or n=3. In the above general formula [II], X represents a silica portion constituting the carrier 1.

In one embodiment of the present invention, the carrier of the column used as the carrier 2 is a resin having a group containing a primary amine, a secondary amine, or/and a tertiary amine. The following general formula [III] is a suitable example of such a resin containing a primary amine and a secondary amine.

[Chem. 3]

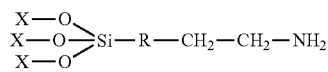

[III]

In the above general formula [III], Y represents a resin portion constituting the carrier 2. In the formula, n is an arbitrary integer, preferably n=1 to 10, more preferably 1 to 8, and even more preferably 1 to 4. The resin constituting the carrier 2 is preferably a hydrophilic resin, and more preferably a resin based on polyvinyl alcohol or modified polyvinyl alcohol. The carrier 2 preferably has a property as an anion exchange resin.

In one embodiment of the present invention, the chromatography column used for separating the acidic sugar chains is a column in which the carrier 1 is packed and a column in which the carrier 2 is packed are connected in series via a flow path. For convenience, when two columns are connected, the column located upstream of the flow path is referred to as a first column, and the column located downstream is referred to as a second column. Here, the first column may be filled with the carrier 1 and the second column may be filled with the carrier 2, or the first column may be filled with the carrier 2 and the second column may be filled with the carrier 1.

A unit in which the second column is connected by a flow path downstream of the outlet of the first column constitutes a chromatography column used for separating acidic sugar chains. It is preferable that the first column and the second column each functions as a hydrophilic interaction chromatography column, hence a chromatography column having a configuration in which the first column and the second column are connected to each other functions as a hydrophilic interaction chromatography column as a whole.

As the chromatography column having the configuration in which the first column and the second column are connected functions as a column for hydrophilic interaction chromatography as a whole, when a sample containing sugar chains is loaded onto a column equilibrated with a mobile phase composed of a hydrophobic solution, the hydrophilic sugar chains are retained on a carrier. And, by gradually replacing the mobile phase with a hydrophilic solution from a hydrophobic one, sugar chains are eluted from the column in descending order of hydrophobicity. Acidic sugar chains are highly hydrophilic because they have sulfate groups, carboxyl groups, phosphate groups, and the like, thus are strongly retained in the column when loaded on a column for hydrophilic interaction chromatography. Therefore, according to the column of the present invention, the acidic sugar chain is selectively held in the column for a longer period of time, the separation capacity of acidic sugar chains is improved, and further, the acidic sugar chain can be analyzed with higher sensitivity by using it.

There are no particular limitation for the mobile phase to be used in the analysis of sugar chains using the chromatography column of the present invention, but the mobile phase in column chromatography is gradually replaced from highly hydrophobic (low hydrophilic) to highly hydrophilic (low hydrophobic). For example, after equilibrating the column with a highly hydrophobic first mobile phase containing about 80% (v/v) acetonitrile, about 2% (v/v) acetic acid, and about 18% (v/v) pure water, and loading the sample to retain the sugar chains on the column, the mobile phase can be gradually replaced with a second highly hydrophilic mobile phase containing about 80% (v/v) pure water, about 5% (v/v) acetic acid, and about 3% (v/v) triethylamine, the pH of which is adjusted to 2-6, so that the sugar chains retained on the column allow to be eluted in order from the lowest hydrophilicity.

The pH of the second mobile phase is particularly important. The pH of the second mobile phase is limited to the acidic side because of the need to coordinate protons to the amino groups of the carrier. By increasing the pH within acidic range, the sulfate group, carboxyl group, phosphate group, and the like contained in acidic sugar chains are dissociated into anions more in the mobile phase, so that they are strongly retained by the carrier having the amino group coordinated with the proton, and the time until they are eluted is prolonged. Therefore, by adjusting the pH of the second mobile phase within the acidic range, the peaks of the acidic sugar chains can be selectively separated. Here, the pH of the second mobile phase is preferably adjusted to pH of 2.0 to 6.0, more preferably to pH of 3.0 to 6.0, even more preferably to pH of 3.5 to 6.0, e.g., pH3.0, 3.5, 4.0, 4.5, 5.0 and a like.

Although the acidic sugar chain can be separated by using the chromatography column of the present invention, in order to detect the separated acidic sugar chain, it is preferable to fluorescently label the sugar chain contained in the sample in advance. Here, the method of fluorescent labeling is not particularly limited, but aminopyridine labeling is suitable. At the reducing end of a sugar or sugar chain, an aldehyde group or a ketone group may be generated when a sugar having a cyclic structure is ring-opened to form a chain structure. In the present invention, 2-aminopyridine labeling (or aminopyridine labeling) refers to producing an imine by reacting the reducing end of a sugar or sugar chain with 2-aminopyridine and subsequently adding 2-aminopyridine to the reducing end of a sugar or sugar chain by reducing the imine with a borane-dimethylamine complex or the like. In the present invention, a 2-aminopyridine labeled sugar chain, an aminopyridine labeled sugar chain, or a labeled sugar chain refers to a sugar or sugar chain labeled with 2-aminopyridine (or labeled with an aminopyridine).

Aminopyridine-labeled sugar chains can be analyzed by loading them onto the chromatography column of the present invention, and continuously irradiating the solution after passing through the column with excitation light by using a fluorescence detector, and measuring the intensity of fluorescence emitted from the effluent. The excitation light thus irradiated is ultraviolet light at a wavelength of 300 to 340 nm, for example, ultraviolet light at a wavelength of 320 nm. The fluorescence thus emitted is measured by a fluorescence detector as ultraviolet light at a wavelength of 300 to 340 nm, for example, as ultraviolet light at a wavelength of 320 nm.

In the present invention, when the acidic sugar chain to be analyzed constitutes a part of the glycoprotein, it is necessary to excise the sugar chain in advance from the glycoprotein before labeling with aminopyridine. The excision of the sugar chain from the glycoprotein is performed by enzyme treatment or chemical treatment. The enzyme treatment is performed using N-glycosidase, glycopeptidase A, O-glycosidase, or the like, and the chemical treatment is performed by hydrazine degradation or the like. By these processes, sugar chains linked to asparagine residues, serine residues, threonine residues, and the like in the glycoprotein are excised.

An example of a method for identifying peaks corresponding to acidic sugar chains on a chromatogram resulting from column chromatography is shown below. At first, the sample is divided, and one part is treated with an enzyme having an activity of cleaving an acidic group contained in the acidic sugar chain from the sugar chain. The sample is then loaded onto column chromatography and the chromatogram obtained by analyzing the sugar chains untreated with the enzyme (enzyme untreated chromatogram) is compared with the chromatogram obtained by analyzing the sugar chains treated with the enzyme (enzyme treated chromatogram), and the peak detected on the enzyme untreated chromatogram but disappearing in the enzyme treated chromatogram can be identified as the peak corresponding to the acidic sugar chains.

Sulfate groups can be cleaved using sulfatase, carboxyl groups can be cleaved using decarboxylase, and phosphate groups can be cleaved using phosphatase from acidic sugar chains, respectively.

Glycoproteins of which the sugar chain is to be analyzed include, but are not limited to, lysosomal enzymes such as iduronate-2-sulfatase, α-galactosidase A, acid sphingomyelinase, α-L-iduronidase, N-acetylgalactosamine-4-sulfatase, glucocerebrosidase (glucosylceramidase), galsulfase, lysosomal acid lipase, acid α-glucosidase, tissue plasminogen activator (t-PA), blood coagulation factor such as blood coagulation factor VII, blood coagulation factor VIII, blood coagulation factor IX, erythropoietin, interferon, thrombomodulin, follicle-stimulating hormones, thyroid-stimulating hormones, GM-CSF, G-CSF, M-CSF, and antibodies, in particular, recombinant glycoproteins of mammals such as human synthesized using recombinant techniques.

Lysosomal enzymes such as iduronate-2-sulfatase and α-galactosidase A have acidic sugar chains modified with mannose-6-phosphate (M6P). Therefore, the sugar chain containing M6P of the lysosomal enzymes can be identified by excising the sugar chain from the lysosome, treating one part of the sugar chain with phosphatase, and comparing the chromatogram between the phosphatase-treated and the untreated chains.

EXAMPLES

While the present invention will be described in further detail below referring to examples, it is not intended that the present invention be limited to the examples.

[Example 1] Preparation of Solutions (a) Sugar Chain Profiling Mobile Phase A:

20 mL of acetic acid was added to 800 mL of acetonitrile and mixed. Then acetonitrile was added to make the volume 1 L. The resulting solution was used as the sugar chain profiling mobile phase A.

(b) Sugar Chain Profiling Mobile Phase B:

50 mL of acetic acid and 30 mL of triethylamine were added to 800 mL of pure water and mixed, and the pH was adjusted by adding 2 M hydrochloric acid. Then pure water was added to make the volume 1 L. The resulting solution was used as the sugar chain profiling mobile phase B. Solutions having pH of 2.5, 3.0, 3.5, and 4.0 were prepared.

[Example 2] Construction of Expression Vectors for hI2S-Humanized Anti-hTfR Antibody Fusion Protein Expression vectors for hI2S-humanized anti-hTfR antibody fusion protein were constructed using genetic sequences coding a humanized anti-hTfR antibody comprising a light chain having the amino acid sequences set forth as SEQ ID NO:1 and a heavy chain having the amino acid sequences set forth as SEQ ID NO:2.

A pEF/myc/nuc vector (Invitrogen Inc.) was digested with KpnI and NcoI to cut out the region containing the EF-1α promoter and its first intron, and the region was blunt-ended with T4 DNA polymerase. A pCI-neo (Invitrogen Inc.) was digested with BglII and EcoRI to cut out the region containing the enhancer/promoter and intron of CMV, and then the region was blunt-ended with T4 DNA polymerase. The above region containing the EF-1α promoter and its first intron was inserted into this to construct a pE-neo vector. The pE-neo vector was digested with SfiI and BstXI and a region of approximately 1 kbp containing the neomycin resistance gene was cut out. Amplification of hygromycin gene was carried out by PCR reaction using primers Hyg-Sfi5' (SEQ ID NO:3) and Hyg-BstX3' (SEQ ID NO:4) and using pcDNA 3.1/Hygro(+)(Invitrogen Inc.) as a template. The amplified hygromycin gene was digested with SfiI and BstXI and inserted into the pE-neo vector from which the above neomycin resistance gene has been cut out to construct a pE-hygr vector.

A DNA fragment (SEQ ID NO:5) containing the gene encoding the full length of the light chain of the humanized anti-hTfR antibody having the amino acid sequence set forth as SEQ ID NO:1 was synthesized. A MluI sequence was introduced on the 5' side of this DNA fragment and a NotI sequence on the 3' side thereof. This DNA fragment was digested with MluI and NotI and incorporated between MluI and Not of the pE-neo vector. The obtained vector was designated pE-hygr(LC) which is a vector for expressing the light chain of humanized anti-hTfR antibody.

A DNA fragment was artificially synthesized, having a nucleotide sequence set forth as SEQ ID NO:7 containing a gene encoding a protein in which hI2S having an amino acid sequence set forth as SEQ ID NO:6 is linked to the C-terminal side of the heavy chain of the humanized anti-hTfR antibody having an amino acid sequence set forth as SEQ ID NO:2 via a linker having an amino acid sequence set forth as (Gly-Ser). This DNA fragment encodes a protein having the amino acid sequence set forth as SEQ ID NO:8, in which a heavy chain of humanized anti-hTfR antibody binds to hI2S. This DNA fragment was digested with MluI and NotI and inserted between MluI and Not of the pE-neo vector to construct pE-neo (HC-I2S).

[Example 3] Preparation of a High Expression Cell Lines of hI2S-Humanized Anti-hTtR Antibody Fusion Proteins CHO cells (CHO-K1 obtained from American Type Culture Collection) were transformed with combinations of pE-hygr (LC) and pE-neo (HC-I2S) constructed in Example 2 using the GenePulser (Bio-Rad Inc.). Transformation of cells was in brief carried out by the following method.

$5 \times 10^5$ CHO-K1 cells were seeded in a 3.5 cm culture dish to which CD OptiCHO™ medium (Thermo Fisher Scientific Inc.) was added and cultured overnight at 37° C. under 5% $CO_2$. After the culture, the cells were suspended in Opti-MEM™ I medium (Thermo Fisher Scientific Inc.) to a density of $5 \times 10^6$ cells/mL. 100 μL of the cell suspension was collected, and thereto 5 μL each of the pE-hygr (LC) and pE-neo (HC-I2S) plasmid DNA solutions both having been diluted to 100 μg/mL with CD OptiCHO™ medium was added. Electroporation was performed using GenePulser (Bio-Rad Inc.) to introduce the plasmids into the cells. After overnight culture under the condition of 37° C., 5% $CO_2$, the cells were selectively cultured in CD OptiCHO™ medium supplemented with 0.5 mg/mL of hygromycin and 0.8 mg/mL of G418.

Then, the cells selected above through the selection culture were seeded on 96-well plates so that not more than one cell might be seeded per well by limiting dilution. The cells then were cultured for about 10 days so that monoclonal colonies formed. Respective culture supernatants of the wells in which monoclonal colony formed were collected, the amount of the humanized antibody contained in culture supernatants was determined by ELISA, and the hI2S-humanized anti-hTfR antibody fusion protein high-expressing cell lines were selected.

The ELISA above was conducted as follows in general. To each well of 96-well microtiter plates (Nunc Inc.) was added 100 μL of a goat anti-human IgG polyclonal antibody solution diluted with 0.05 M sodium bicarbonate buffer (pH 9.6) to 4 μg/mL, and the plate was left to stand for at least one hour at room temperature so as to allow the antibody to be adsorbed by the plates. Then, after each well was washed three times with a phosphate-buffered saline (pH 7.4) supplemented with 0.05% Tween20 (PBS-T), 200 μL of Starting Block (PBS) Blocking Buffer (Thermo Fisher Scientific Inc.) was added to each well, and the plates were left to stand for 30 minutes at room temperature. After each well was washed with PBS-T three times, the culture supernatant or the human IgG reference standard product which had been diluted with a phosphate buffer saline (pH 7.4) supplemented with 0.5% BSA and 0.05% Tween20 (PBS-BT) to appropriate concentrations, was added to each well, in the amount of 100 μL, and the plates were left to stand for at least one hour at room temperature. After the plates were washed three times with PBS-T, 100 μL of HRP-labeled anti-human IgG polyclonal antibody solution which had been diluted with PBS-BT, was added to each well, and the plates were left to stand for at least one hour at room temperature. After the wells were washed three times with PBS-T, citrate-phosphate buffer (pH 5.0) containing 0.4 mg/mL o-phenylenediamine was added to each well, in the amount of 100 μL, and the wells were left to stand for 8 to 20 minutes at room temperature. Then, 1 mol/L sulfuric acid was added to each well in the amount of 100 μL to terminate the reaction, and the absorbance for each well was measured at 490 nm using a 96-well plate reader. The cells corresponding to the wells which exhibited the higher measurements were regarded as a high-expressing cell line for hI2S-humanized anti-hTfR antibody fusion protein. The hI2S-humanized anti-hTfR antibody fusion protein expressed by this cell line was designated as I2S-anti-hTfR antibody.

[Example 4] Culture of hI2S-Anti-hTfR Antibody Expressing Strain

The hI2S-anti-hTfR antibodies were produced by the method described below. The hI2S-anti-hTfR antibody expressing strain obtained in Example 3 was suspended in about 200 L of serum-free medium (EX-CELL Advanced CHO Fed-batch Medium, Sigma Aldrich Inc.) containing 4 mM L-alanyl-L-glutamine, 100 μmol/L hypoxanthine and 16 μmol/L thymidine to the density of about 2×10⁵ cells/mL. 140 L of this cell suspension was transferred to a culture tank. The cells were cultured for about 11 days at a temperature range of 34 to 37° C., while the medium was stirred with an impeller, and the dissolved oxygen saturation of the medium was kept at about 40%. During the culture period, glucose concentration of the medium was monitored. When the glucose concentration of the medium became less than 15 mmol/L, the glucose solution was immediately added to the medium so that the glucose concentration became 36 mmol/L. After completion of the culture, the medium was collected. The recovered medium was filtered with Millistak+HC Pod Filter grade D0HC (Merck Inc.) and further filtered with Millistak+HC Pod Filter (grade X0HC (Merck Inc.) to obtain a culture supernatant containing I2S-anti-hTfR antibody. The culture supernatant was subjected to ultrafiltration using a Pellicon™ 3 Cassette w/Ultracel PLCTK Membrane (pore size: 30 kDa, membrane area: 1.14 m², Merck Inc.). The concentrate was then filtered using OpticapXL600 (0.22 μm, Merck Inc.). The obtained solution was used as a concentrated culture supernatant.

[Example 5] Purification of hI2S-Anti-hTfR Antibody

The concentrated culture supernatant was filtrated by a Millipak-200 Filter Unit (pore size: 0.22 μm, Merck Inc.) after adding thereto 20 mM Tris-HCl buffer (pH 7.0) containing 0.5 volume of 140 mM NaCl. The solution after filtration was loaded onto a MabSelect SuRe LX column (column volume: about 3.2 L, bed height: about 20 cm, GE Healthcare Inc.), which was a protein A affinity column, and equilibrated with 4 column volumes of 20 mM Tris-HCl buffer (pH 7.0) containing 140 mM NaCl, at a constant flow rate of 200 cm/hour to adsorb I2S-anti-hTfR antibody to protein A.

Subsequently, the column was washed with 5 column volumes of 10 mM Tris-HCl buffer (pH 7.0) containing 500 mM NaCl and 450 mM arginine at the same flow rate. Then the column was further washed with 2.5 column volumes of 20 mM Tris-HCl buffer (pH 7.0) containing 140 mM NaCl at the same flow rate. Then I2S-anti-hTfR antibody 3 adsorbed to Protein A was eluted with 5 column volumes of 100 mM glycine buffer (pH 3.5) containing 140 mM NaCl. The eluate was immediately neutralized by 1 M Tris-HCl buffer (pH 7.5).

To the above eluate from the Protein A affinity column, 200 mM phosphate buffer (pH 7.0), 10 mM MES buffer (pH 7.3) containing 4 M NaCl and 2 mM phosphate buffer, and 1 M Tris-HCl buffer solution (pH 8.0) were added in the order, and the concentrations of sodium phosphate and NaCl contained in the eluate were adjusted to 2 mM and 215 mM, respectively, and the pH of the eluate was adjusted to 7.3. The eluate was then filtered through Opticap XL 600 (pore size: 0.22 μm, Merck Inc.). The solution after filtration was applied to a CHT Type II 40 μm column, a hydroxyapatite column (Column volume: about 3.2 L, bed height: about 20 cm, Bio-Rad Inc.), equilibrated with 4 column volumes of 10 mM MES buffer solution (pH 7.3) containing 215 mM NaCl and 2 mM sodium phosphate at a constant flow rate of 200 cm/hour to adsorb I2S-anti-hTfR antibody to hydroxyapatite.

Subsequently, the column was washed with 5 column volumes of the same buffer at the same flow rate. Then I2S-anti-hTfR antibody 3 adsorbed on hydroxyapatite was eluted with 5 column volumes of 35 mM phosphate buffer (pH 7.3) containing 215 mM NaCl.

To the above eluate from the hydroxyapatite column, dilute hydrochloric acid was added to adjust the pH to 6.5. Then, ultrafiltration was carried out using Pellicon™ 3 Cassette w/Ultracel PLCTK Membrane (pore size: 30 kDa, membrane area: 1.14 m², Merck Inc.) to concentrate I2S-antihTfR antibody 3 in the solution at the concentration of about 2 mg/mL. The concentrate was then filtered using Opticap XL 600 (0.22 μm, Merck Inc.).

The above concentrated solution was applied to a Superdex 200 column, size exclusion column (column volume: about 12.6 L, bed height: 40 cm, GE Healthcare Inc.) equilibrated with 5 column volumes of 20 mM phosphate buffer (pH 6.5) containing 0.8 mg/mL NaCl and 75 mg/mL sucrose at a constant flow rate of 19 cm/hr, and the same buffer was supplied at the same flow rate. At this time, an absorbance photometer for continuously measuring the absorbance of the eluate was placed in the flow path of the eluate from the size exclusion column, and the absorbance at 280 nm was monitored. The fractions which corresponded to an absorption peak at 280 nm were collected as a fractions containing I2S-anti-hTfR antibody, which was designated as a purified product of I2S-anti-hTfR antibody (hereinafter, I2S-anti-hTfR antibody).

[Example 6] Reductive Alkylation of hI2S-Anti hTfR Antibodies 0.2 mg of the I2S-anti hTfR antibody obtained in Example 5 above was collected and dried under reduced pressure, dissolved in 50 μl of a protein lysis solution (a solution prepared by dissolving 66.8 g of guanidine hydrochloride, 6.1 g of tris(hydroxymethyl)aminomethane and 0.372 g of disodium ethylenediamine tetraacetate in water, adjusted to pH 8.5 with 1 N hydrochloric acid, and adding water to make the volume 100 mL). 4 μL of the reduction solution (10 mg of dithiothreitol dissolved in 50 μL of protein lysate) was then added, shaken, and allowed to stand at room temperature for 30 minutes. Then, 4 μL of iodoacetic acid solution (25 mg of iodoacetic acid dissolved in 60 μL of 1 N aqueous sodium hydroxide solution) was added, shaken, and allowed to stand at room temperature for 30 minutes under light shielding. The reactant was then subjected to gel-filtration column chromatography to separate fractions containing I2S-anti hTfR antibody. At this time, the gel-filtration column chromatography was carried out by applying the reactant to a Sephadex (registered trademark) G-25 superfine (column diameter: 5 mm, column length: 150 mm, GE Healthcare Inc.) equilibrated with pure water, flowing water at a flow rate of 1 mL/min at room temperature, and monitoring the absorbance at a wavelength of 215 nm with an ultraviolet absorbance spectrophotometer. The fraction containing I2S-anti hTfR antibody was separated and dried under reduced pressure.

[Example 7] Trypsinization

To the reductively alkylated I2S-anti hTfR antibody dried under reduced pressure obtained in Example 6 above, 70 μl of 70 mmol/L ammonium bicarbonate aqueous solution was added and shaken. Then 10 μL of trypsin solution (25 μg of trypsin dissolved in 50 mL of 1 mmol/L hydrochloric acid) was added, shaken, and allowed to stand at 2 to 8 degrees for 9 hours for reaction. The solution was then heated at 95 degrees for 5 minutes to inactivate trypsin. The resulting solution was used as a trypsin digest.

[Example 8] Glycosidase Treatment

To the reactant of trypsinization obtained in Example 7 above, 5 μL of a glycosidase solution (N-glycosidase dissolved in pure water at a concentration of 1,000 units/mL) was added, and the solution was allowed to stand at degrees for 3 hours for reaction. The solution was then heated at degrees for 5 minutes to deactivate the glycosidase. The resulting solution was used as a glycosidase digest.

[Example 9] Aminopyridine-labeling of Sugar Chains

To the reactant of glycosidase digest obtained in Example 8 above, 20 μL of a 2-aminopyridine solution (150 mg of 2-aminopyridine dissolved in 50 μL of acetic acid) was added, shaken, and reacted at 80 degrees for 1 hour. Then, 20 μL of borane-dimethylamine complex solution (20 mg of borane-dimethylamine complex dissolved in 100 μL of acetic acid) was added, shaken, and reacted at 80 degrees for 1 hour. Then, 100 μL of toluene was added, shaken, and then centrifuged to precipitate sugar chains and remove the upper layer, i.e. the toluene layer. This extraction process with toluene was repeated two more times to remove unreacted 2-aminopyridine. In the last toluene extraction process, solution was removed as much as possible with a precipitate left. The solution containing toluene removed in this process was collected in a container for disposal of an organic solvent. Then the precipitated sugar chain was dried under reduced pressure, dissolved in 50 μL of water to form a sugar chain dissolving solution. The sugar chain dissolving solution was subjected to gel filtration column chromatography to separate a fraction containing an aminopyridine-labeled sugar chain.

At this time, the gel filtration column chromatography was carried out by applying a sugar chain dissolving solution and subsequently 0.1% (v/v) acetic acid aqueous solution to SEPHADEX™ G-15 (column inner diameter: 28 mm, column length: 200 mm, GE Healthcare Inc.) equilibrated with pure water at flow rate of 8 mL/min at room temperature, with the fluorescence intensity monitored with a fluorescence detector (excitation wavelength: 320 nm, fluorescence wavelength: 400 nm). The fractions corresponding to the peak appearing between 5 and 10 minutes after applying the sugar chain dissolving solution onto the column, were collected as a fraction containing aminopyridine-labeled sugar chains. The collected fractions were dried under reduced pressure.

[Example 10] Alkaline Phosphatase (BAP) Treatment 1 mL of pure water was added to the dried product obtained in Example 9 under reduced pressure and the product was dissolved. This solution was dispensed into two 0.5 mL tubes, dried under reduced pressure, and dissolved in 80 μL of pure water. To a new tube, 52 μL of the lysis solution was dispensed. In this tube, 1 unit of alkaline phosphatase (Takara Bio Inc.) and 6 μL of reaction buffer (500 mM Tris-HCl (pH 9.0) containing 10 mM $MgCl_2$) was added and mixed, and the mixture was allowed to react at 50 degrees for 1 hour. To 30 μL of the solution after the reaction, 75 μL of the sugar chain profiling mobile phase A (prepared in Example 1) was added and mixed. This solution was used as an alkaline phosphatase treated sample (BAP-treated sample). To another new tube, 52 μL of the lysis solution was dispensed, and to this tube 2 μL of pure water and 6 μL of reaction buffer (500 mM Tris-HCl (pH 9.0) containing 10 mM MgCl2) were added and mixed, and the mixture was allowed to react at degrees for 1 hour. To 30 μL of the solution after the reaction, 75 μL of the sugar chain profiling mobile phase A was added and mixed. This solution was used as an alkaline phosphatase (BAP) untreated sample (BAP-untreated sample).

[Example 11] Separating and Analyzing Acidic Sugar Chains

The BAP-treated sample and the BAP-untreated sample obtained in Example 10 were loaded onto a column under the following conditions (column chromatography condition 1 and column chromatography condition 2), and the sugar chains contained in each sample were separated and analyzed. Sugar chain profiling mobile phase A and sugar chain profiling mobile phase B were prepared in Example 1. Asahipak™ NH2P-50 4E is a hydrophilic interaction chromatography column (normal phase chromatography column) using a resin based on polyvinyl alcohol into which an amino group is introduced as a functional group as a carrier. TSKgel NH2-100 is a hydrophilic interaction chromatography column (normal phase chromatography column) using silica having a surface modified to be hydrophobic on which an aminoalkyl group introduced as a functional group as a carrier.

TABLE 1 column chromatography condition 1

| | |
|---|---|
| Column | Asahipak NH2P-50 4E (inner diameter: 4.6 mm, length: 250 mm, particle size: 5 μm; Showa Denko, Inc.) |
| Sample load volume | 30 μL |
| Column temperature | 50° C. |
| Flow rate | 0.6 mL/min (constant rate) |

| Time after sample load (min) | Sugar chain mobile phase A (volume %) | Sugar chain mobile phase B (volume %) |
|---|---|---|
| 0~2 | 70 | 30 |
| 2.01~80 | 70→5 (linear gradient) | 30→95 (linear gradient) |
| 80.01~105 | 5 | 95 |
| 105.01~140 | 70 | 30 |

TABLE 2 column chromatography condition 2

| | |
|---|---|
| Column | Column unit in which Asahipak NH2P-50 4E (inner diameter: 4.6 mm, length: 250 mm, particle size: 5 μm; Showa Denko, Inc.) is directly connected downstream of TSKgel NH2-100 (inner diameter: 4.6 mm, length: 50 mm, particle size: 3 μm; TOSOH, Inc.) |
| Sample load volume | 30 μL |
| Column temperature | 50° C. |
| Flow rate | 0.6 mL/min (constant rate) |

| Time after sample load (min) | Sugar chain mobile phase A (volume %) | Sugar chain mobile phase B (volume %) |
|---|---|---|
| 0~2 | 70 | 30 |
| 2.01~80 | 70→5 (linear gradient) | 30→95 (linear gradient) |
| 80.01~105 | 5 | 95 |
| 105.01~140 | 70 | 30 |

In both column chromatography condition 1 and column chromatography condition 2, the column was equilibrated by flowing at a flow rate of 0.6 mL/min a mobile phase containing sugar chain profiling mobile phase A and sugar chain profiling mobile phase B in a proportion of 70% and 30% by volume.

Column chromatography was also performed by setting a column in the Shimadzu HPLC Systems LC-20A (Shimadzu Corporation), heating the column to 50 degrees in a column oven, installing a fluorescent detector downstream of the column outlet, and irradiating the solution after passing through the column with ultraviolet light at a wavelength of 320 nm as the excitation light to detect fluorescence at a wavelength of 400 nm.

[Example 12] Results of Acidic Sugar Chain Analyses

At first, acidic sugar chains were separated and analyzed by the method shown in Example 11 using the sugar chain profiling mobile phase B adjusted to pH 2.5. The results are shown in FIG. 1. Comparing the chromatograms of the BAP-treated sample (chromatogram A in FIG. 1) and the BAP-untreated sample (chromatogram B in FIG. 1) under column chromatography condition 1 (chromatography condition 1), there are peaks, peaks 1 and 2, which can be confirmed in the chromatogram of BAP-untreated sample but cannot be confirmed in the chromatogram of BAP-treated sample. These peaks correspond to monophosphorylated sugar chains and diphosphorylated sugar chains, respectively. Since the phosphate group is released from the sugar chain by the BAP treatment, these peaks disappear in the chromatogram of BAP-treated sample. When comparing the chromatograms of the BAP-treated sample (chromatogram C in FIG. 1) and the BAP-untreated sample (chromatogram D in FIG. 1) in column chromatography condition 2 (chromatography condition 2), as similar to the result of column chromatography condition 1, there are peaks, peaks 1 and 2, which correspond to monophosphorylated sugar chains and dephosphorylated sugar chains, respectively, which can be confirmed with the chromatogram of BAP-untreated sample but not with the chromatogram of BAP-treated sample. In the column chromatography condition 2, the elution times on which the peaks 1 and 2 appeared tend to be prolonged than those in the column chromatography condition 1.

Figure 2:
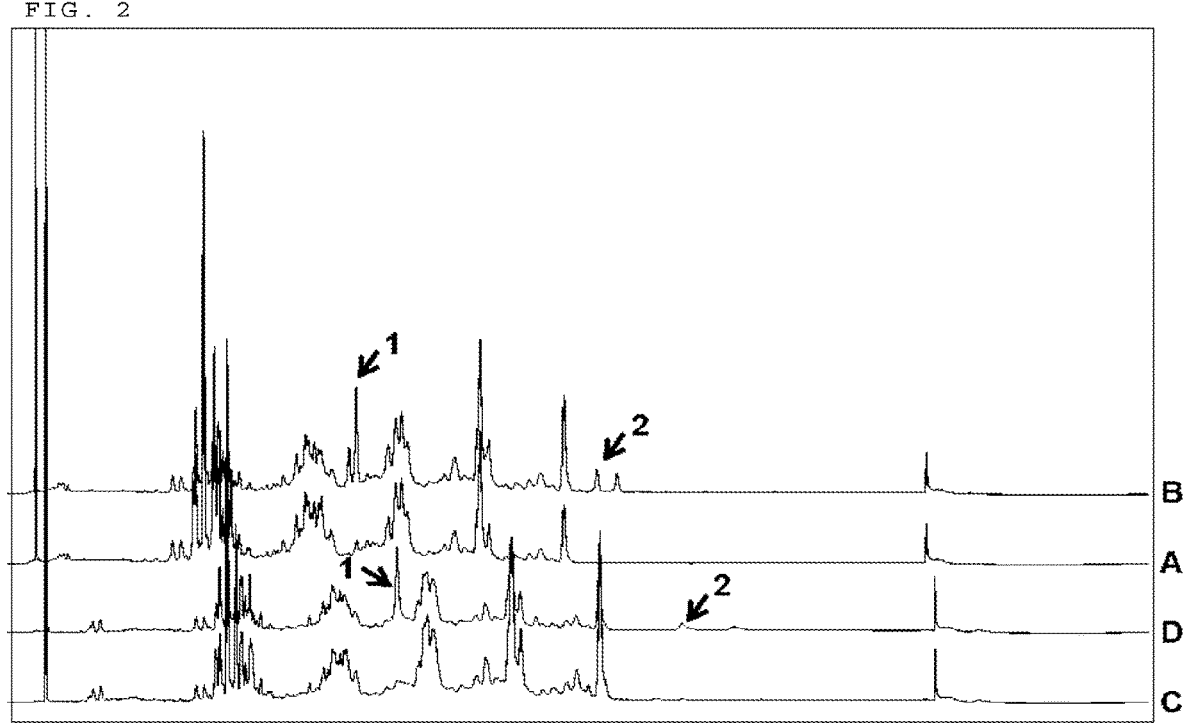
FIG. 2 shows the results of analysis of acidic sugar chains using the sugar chain profiling mobile phase B adjusted to pH 3.0. In the figure, "A" represents a chromatogram obtained by analyzing a BAP-treated sample under column chromatography condition 1 (chromatography condition 1), "B" represents a chromatogram obtained by analyzing a BAP-untreated sample under chromatography condition 1, "C" represents a chromatogram obtained by analyzing a BAP-treated sample under column chromatography condition 2 (chromatography condition 2), and "D" represents a chromatogram obtained by analyzing a BAP-untreated sample under chromatography condition 2, respectively. Arrows 1 and 2 indicate peaks corresponding to phosphorylated sugar chains. The vertical axis represents the fluorescence intensity (400 nm) and the horizontal axis represents the retention time, respectively.

Then, acidic sugar chains were separated and analyzed by the method shown in Example 11 using the sugar chain profiling mobile phase B adjusted to pH 3.0. The results are shown in FIG. 2. Comparing the chromatograms of the BAP-treated sample (chromatogram A in FIG. 2) and the BAP-untreated sample (chromatogram B in FIG. 2) under column chromatography condition 1, there are peaks 1 and 2 which can be confirmed in the chromatogram of BAP-untreated sample but cannot be confirmed in the chromatogram of BAP-treated sample. As similar to FIG. 1, each of these peaks corresponds to monophosphorylated sugar chains and diphosphorylated sugar chains. When comparing the chromatograms of BAP-treated sample (Chromatogram C in FIG. 2) and BAP-untreated sample (chromatogram D in FIG. 2) in column chromatography condition 2, as in column chromatography condition 1, there are peaks 1 and 2, which correspond to monophosphorylated sugar chains and diphosphorylated chains, respectively, which can be confirmed with the chromatogram of BAP-untreated sample but not with the chromatogram of BAP-treated sample. When compared with the column chromatography condition 1, in the column chromatography condition 2, the elution times on which the peaks 1 and 2 appeared tend to be prolonged than those when using the sugar chain profiling mobile phase B adjusted to pH 2.5.

Figure 3:
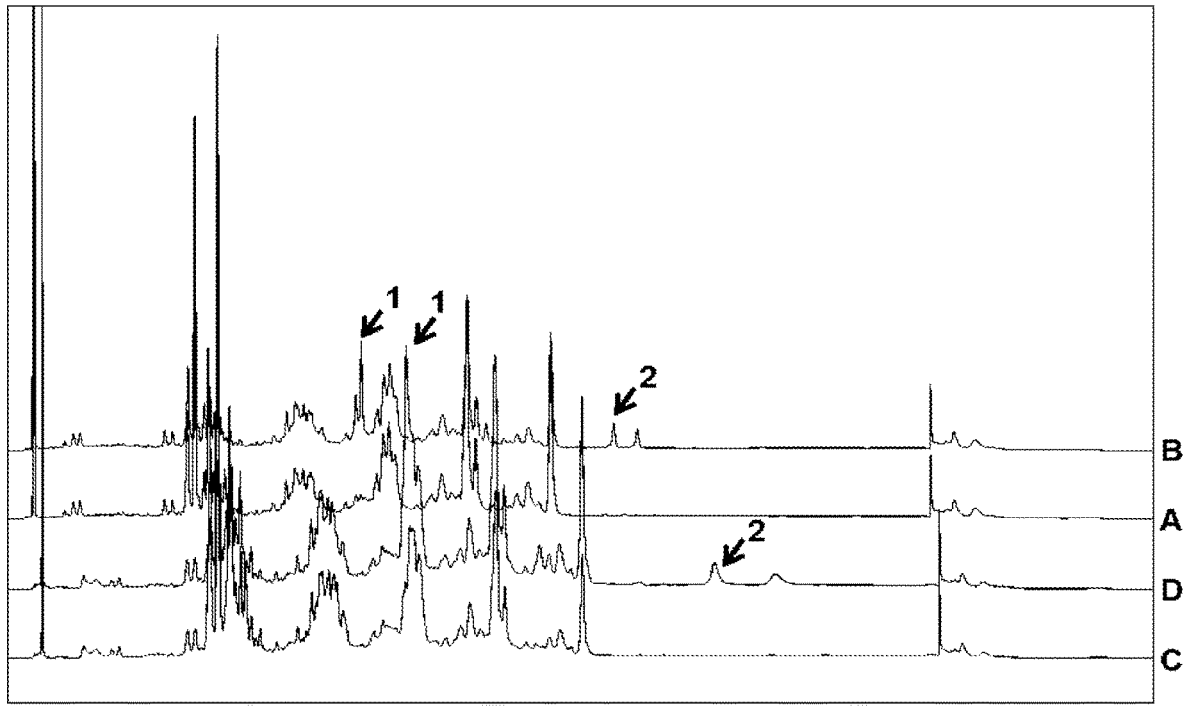
FIG. 3 shows the results of analysis of acidic sugar chains using the sugar chain profiling mobile phase B adjusted to pH 3.5. In the figure, "A" represents a chromatogram obtained by analyzing a BAP-treated sample under column chromatography condition 1 (chromatography condition 1), "B" represents a chromatogram obtained by analyzing a BAP-untreated sample under chromatography condition 1, "C" represents a chromatogram obtained by analyzing a BAP-treated sample under column chromatography condition 2 (chromatography condition 2), and "D" represents a chromatogram obtained by analyzing a BAP-untreated sample under chromatography condition 2, respectively. Arrows 1 and 2 indicate peaks corresponding to phosphorylated sugar chains. The vertical axis represents the fluorescence intensity (400 nm) and the horizontal axis represents the retention time, respectively.

Further, acidic sugar chains were separated and analyzed by the method shown in Example 11 using the sugar chain profiling mobile phase B adjusted to pH 3.5. The results are shown in FIG. 3. Comparing the chromatograms of the BAP-treated sample (chromatogram A in FIG. 3) and the BAP-untreated sample (chromatogram B in FIG. 3) under column chromatography condition 1, there are peaks, peaks 1 and 2, which can be confirmed in the chromatogram of BAP-untreated sample but cannot be confirmed in the chromatogram of BAP-treated sample. As similar to FIGS. 1 and 2, these peaks correspond to monophosphorylated sugar chains and diphosphorylated sugar chains, respectively. Then, comparing the chromatograms of the BAP-treated sample (Chromatogram C in FIG. 3) and the BAP-untreated sample (chromatogram D in FIG. 3) in column chromatography condition 2, as similar to in column chromatography condition 1, there are peaks 1 and 2, which correspond to monophosphorylated sugar chains and diphosphorylated chains, respectively, which can be confirmed with the chromatogram of BAP-untreated sample but not with the chromatogram of BAP-treated sample. When compared with the column chromatography condition 1, in the column chromatography condition 2, the elution times on which the peaks 1 and 2 appeared tend to be prolonged than those when using the sugar chain profiling mobile phase B adjusted to pH 3.0.

Figure 4:
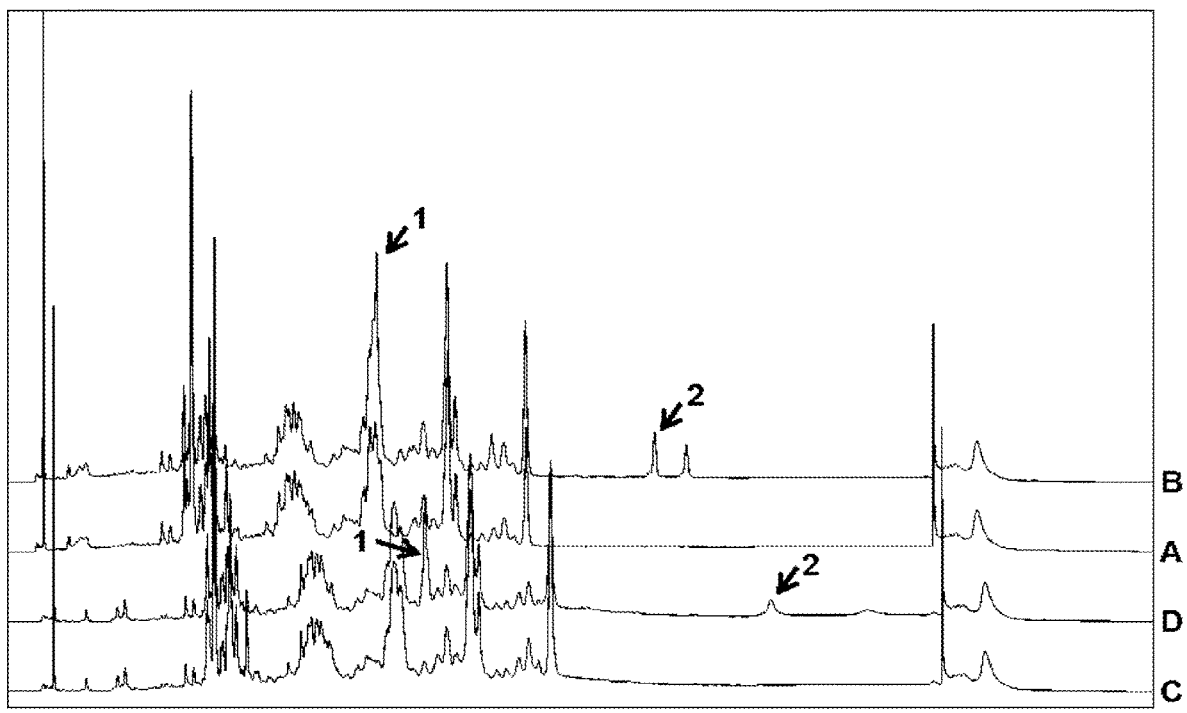
FIG. 4 shows the results of analysis of acidic sugar chains using the sugar chain profiling mobile phase B adjusted to pH 2.5. In the figure, "A" represents a chromatogram obtained by analyzing a BAP-treated sample under column chromatography condition 1 (chromatography condition 1), "B" represents a chromatogram obtained by analyzing a BAP-untreated sample under chromatography condition 1, "C" represents a chromatogram obtained by analyzing a BAP-treated sample under column chromatography condition 2 (chromatography condition 2), and "D" represents a chromatogram obtained by analyzing a BAP-untreated sample under chromatography condition 2, respectively. Arrows 1 and 2 indicate peaks corresponding to phosphorylated sugar chains. The vertical axis represents the fluorescence intensity (400 nm) and the horizontal axis represents the retention time, respectively.

Further, acidic sugar chains were separated and analyzed by the method shown in Example 11 using the sugar chain profiling mobile phase B adjusted to pH 4.0. The results are shown in FIG. 4. Comparing the chromatograms of the BAP-treated sample (chromatogram A in FIG. 4) and the BAP-untreated sample (chromatogram B in FIG. 4) under column chromatography condition 1, there are peaks, peaks 1 and 2, which can be confirmed in the chromatogram of BAP-untreated sample but cannot be confirmed in the chromatogram of BAP-treated sample. As in FIGS. 1 to 3, these peaks correspond to monophosphorylated sugar chains and diphosphorylated sugar chains, respectively. When comparing the chromatograms of the BAP-treated sample (Chromatogram C in FIG. 4) and the BAP-untreated sample (chromatogram D in FIG. 4) in column chromatography condition 2, as similar to column chromatography condition 1, there are peaks, peaks 1 and 2, which correspond to monophosphorylated sugar chains and diphosphorylated chains, respectively, which can be confirmed with the chromatogram of BAP-untreated sample but not with the chromatogram of BAP-treated sample. In the column chromatography condition 2, the elution times on which the peaks 1 and 2 appeared tend to be prolonged than those in the column chromatography condition 1.

The results above show that when acidic sugar chains are analyzed under the column chromatography condition 2, the retention time until the acidic sugar chain is eluted is selectively lengthened, and the acidic sugar chains are more clearly separated from each other, resulting that the acidic sugar chains contained in sugar chains can be detected with higher sensitivity. Thus it can be concluded that the acidic sugar chains contained in the sugar chains can be detected with higher sensitivity by combining a hydrophilic interaction chromatography column (normal phase column chromatography column) using a resin, the based on polyvinyl alcohol into which an amino group is introduced as a functional group, as a carrier, and a hydrophilic interaction chromatography column (normal phase column chromatography column) using silica having a surface modified to be hydrophobic on which an aminoalkyl group introduced as a functional group as a carrier.

INDUSTRIAL APPLICABILITY

According to the present invention, it is possible to provide a chromatography column capable of analyzing acidic sugar chains, for example acidic sugar chains excised from glycoproteins by an enzyme, with high sensitivity, and a method for analyzing acidic sugar chains using the column.

SEQUENCE LISTING FREE TEXT

SEQ ID NO: 1: Amino acid sequence of the light-chain of humanized anti-hTfR antibody SEQ ID NO: 2: Amino acid sequence of the heavy-chain of humanized anti-hTfR antibody SEQ ID NO:3: Primer Hyg-Sfi5', synthetic sequence SEQ ID NO:4: Primer Hyg-BstX3', synthetic sequence SEQ ID NO:5: Nucleic acid sequence containing nucleic acid sequence encoding the light-chain of humanized anti-hTfR antibody, synthetic sequence SEQ ID NO:7: Nucleotide sequence encoding the fused protein of the heavy-chain of humanized anti-hTfR antibody and hI2S, synthetic sequence SEQ ID NO: 8: Amino acid sequence of fused protein of the heavy-chain of humanized anti-hTfR antibody and hI2S

The invention claimed is:

1. Method for separating an acidic sugar chain from a sample, the method comprising:
    labeling the acidic sugar chain in the sample with an aminopyridine;
    subjecting the sample comprising an aminopyridine-labeled acidic sugar chain to chromatography on a chromatography column, the chromatography column comprising a first column having an outlet, and a second column connected downstream of the outlet of the first column, wherein the first column comprises a carrier 1 which is hydrophobically modified silica having a group comprising at least one of a primary amine, a secondary amine and a tertiary amine, and the second column comprises a carrier 2 which is a resin having an amino group of the following formula III:

Y—NH(CH$_2$CH$_2$NH)$_n$H,    formula III where Y represents a resin portion of the carrier 2, and n is an integer of 1 to 8;
    continuously directing an effluent from the chromatography column to a flow path;
    continuously measuring fluorescence intensity of the effluent flowing in the flow path; and
    identifying a peak of fluorescence intensity corresponding to the acidic sugar chain in an obtained chromatogram,
    wherein the subjecting of the sample to the chromatography comprises passing a first mobile phase through the chromatography column and thereafter passing a second mobile phase through the chromatography column, wherein the second mobile phase has hydrophobicity lower than hydrophobicity of the first mobile phase.

2. The method according to claim 1, wherein the acidic sugar chain is from a glycoprotein in the sample.

3. The method according to claim 2, wherein the glycoprotein is a lysosomal enzyme.

4. The method according to claim 1, wherein the first column and the second column are hydrophilic interaction chromatography columns.

5. The method according to claim 1, wherein the carrier 2 is an anion exchange resin.

6. The method according to claim 1, wherein the carrier 1 has a hydrophobic group of the following formula I and an amino group of the following formula II:

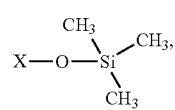
formula I
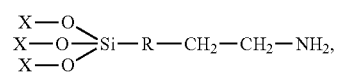
formula II
wherein in the formula I, X represents a silica portion of the carrier 1, and
in the formula II, X represents the silica portion of the carrier 1, and R represents an alkyl of $-(CH_2)_n-$ where $n=1-8$.
7. The method according to claim 1, wherein the resin is made from a polyvinyl alcohol.
* * * * *

```
                              SEQUENCE LISTING

Sequence total quantity: 8
SEQ ID NO: 1            moltype = AA  length = 219
FEATURE                 Location/Qualifiers
REGION                  1..219
                        note = amino acid sequence of the light-chain of humanized
                         anti-hTfRantibody
source                  1..219
                        mol_type = protein
                        organism = synthetic construct
SEQUENCE: 1
DIVMTQTPLS LSVTPGQPAS ISCRSSQSLV HSNGNTYLHW YLQKPGQSPQ LLIYKVSNRF    60
SGVPDRFSGS GSGTDFTLKI SRVEAEDVGV YYCSQSTHVP WTFGQGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 2            moltype = AA  length = 448
FEATURE                 Location/Qualifiers
REGION                  1..448
                        note = amino acid sequence of the heavy-chain of humanized
                         anti-hTfRantibody
source                  1..448
                        mol_type = protein
                        organism = synthetic construct
SEQUENCE: 2
EVQLVQSGAE VKKPGESLKI SCKGSGYSFT NYWLGWVRQM PGKGLEWMGD IYPGGDYPTY    60
SEKFKVQVTI SADKSISTAY LQWSSLKASD TAMYYCARSG NYDEVAYWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP APIEKTISKA KGQPREPQVY TLPPSRDELT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPGK                                     448

SEQ ID NO: 3            moltype = DNA  length = 20
FEATURE                 Location/Qualifiers
misc_feature            1..20
                        note = Primer Hyg-Sfi5', synthetic sequence
source                  1..20
                        mol_type = other DNA
                        organism = synthetic construct
SEQUENCE: 3
gaggccgcct cggcctctga                                               20

SEQ ID NO: 4            moltype = DNA  length = 29
FEATURE                 Location/Qualifiers
misc_feature            1..29
                        note = Primer Hyg-BstX3', synthetic sequence
source                  1..29
                        mol_type = other DNA
                        organism = synthetic construct
SEQUENCE: 4
aaccatcgtg atgggtgcta ttcctttgc                                     29
```

```
SEQ ID NO: 5              moltype = DNA   length = 740
FEATURE                   Location/Qualifiers
misc_feature              1..740
                          note = Nucleic acid sequence containing nucleic acid
                            sequenceencoding the light-chain of humanized anti-hTfR
                            antibody,synthetic sequence
source                    1..740
                          mol_type = other DNA
                          organism = synthetic construct
SEQUENCE: 5
acgcgtgccg ccaccatggg ctggagctgg attctgctgt tcctcctgag cgtgacagca   60
ggagtgcaca gcgacatcgt gatgacccag actcccctga gcctgagcgt gacacctggc  120
cagcctgcca gcatcagctg cagaagctct cagagccctg tgcacagcaa cggcaacacc  180
tacctgcact ggtatctgca gaagcccggc cagagccctc agctgctgat ctacaaggtg  240
tccaacagat tcagcggcgt gcccgacaga ttctccggca gcggctctgg caccgacttc  300
accctgaaga tttccagagt ggaagccgag gacgtgggcg tgtactactg cagccagagc  360
acccacgtgc cctggacatt cggccagggc accaaggtgg aaatcaagag aaccgtggcc  420
gctcccagcg tgttcatctt cccaccta gc gacgagcagc tgaagtccgg cacagcctct  480
gtcgtgtgcc tgctgaacaa cttctacccc cgcgaggcca aggtgcagtg gaaggtggac  540
aacgccctgc agagcggcaa cagccaggaa agcgtgaccg agcaggactc caaggacagc  600
acctacagcc tgagcagcac cctgaccctg agcaaggcct actacgagaa gcacaaggtg  660
tacgcctgcg aagtgaccca ccagggcctg tctagccccg tgaccaagag cttcaacaga  720
ggcgagtgct aagcggccgc                                              740

SEQ ID NO: 6              moltype = AA   length = 525
FEATURE                   Location/Qualifiers
source                    1..525
                          mol_type = protein
                          organism = Homo sapiens
SEQUENCE: 6
SETQANSTTD ALNVLLIIVD DLRPSLGCYG DKLVRSPNID QLASHSLLFQ NAFAQQAVCA   60
PSRVSPLTGR RPDTTRLYDF NSYWRVHAGN FSTIPQYFKE NGYVTMSVGK VFHPGISSNH  120
TDDSPYSWSF PPYHPSSEKY ENTKTCRGPD GELHANLLCP VDVLDVPEGT LPDKQSTEQA  180
IQLLEKMKTS ASPFFLAVGY HKPHIPFRYP KEFQKLYPLE NITLAPDPEV PDGLPPVAYN  240
PWMDIRQRED VQALNISVPY GPIPVDFQRK IRQSYFASVS YLDTQVGRLL SALDDLQLAN  300
STIIAFTSDH GWALGEHGEW AKYSNFDVAT HVPLIFYVPG RTASLPEAGE KLFPYLDPFD  360
SASQLMEPGR QSMDLVELVS LFPTLAGLAG LQVPPRCPVP SFHVELCREG KNLLKHFRFR  420
DLEEDPYLPG NPRELIAYSQ YPRPSDIPQW NSDKPSLKDI KIMGYSIRTI DYRYTVWVGF  480
NPDEFLANFS DIHAGELYFV DSDPLQDHNM YNDSQGGDLF QLLMP                 525

SEQ ID NO: 7              moltype = DNA   length = 3008
FEATURE                   Location/Qualifiers
misc_feature              1..3008
                          note = Nucleotide sequence encoding the fused protein of
                            theheavy-chain of humanized anti-hTfR antibody and
                            hI2S,synthetic sequence
source                    1..3008
                          mol_type = other DNA
                          organism = synthetic construct
SEQUENCE: 7
acgcgtgccg ccaccatggg ctggagctgg attctgctgt tcctcctgag cgtgacagca   60
ggagtgcaca gcgaggtgca actagtgcag tctggagcag aggtgaaaaa gcccggggag  120
tctctgaaga tcagctgtaa gggttctgga tacagctttt tgaactactg gctgggatgg  180
gtgcgccaga tgcccgggaa aggcctggag tggattgggg acatctaccc cggcggagac  240
tacctacat acagcgagaa gttcaaggtc aaggccatca tctcagccga cacgtccatc  300
agcaccgtct acctgcagtt gagcagcctg aaggctcgg acaccgccat gtatttctgt  360
gcgagatcag gcaattacga cgaagtggc tactggggcc aaggaaccct ggtcaccgtc  420
tcctcagcta gcaccaaggg cccatcggtc ttcccctgg caccctcctc aagagcacc  480
tctggggca cagcggccct gggctgcctg gtcaaggact acttccccga accggtgacg  540
gtgtcgtgga actcaggcgc cctgaccagc ggcgtgcaca ccttcccggc tgtcctacag  600
tcctcaggac tctactccct cagcagcgtg gtgaccgtgc cctccagcag cttgggcacc  660
cagacctaca tctgcaacgt gaatcacaag cccagcaaca ccaaggtgga caagaaagtt  720
gagcccaaat cttgtgacaa aactcacacg tgcccaccgt gcccagcacc tgaactcctg  780
gggggtccgt cagtcttcct cttcccccca aaacccaagg acaccctcat gatctcccgg  840
acccctgagg tcacatgcgt ggtggtggac gtgagccacg aagaccctga ggtcaagttc  900
aactggtacg tggacggcgt ggaggtgcat aatgccaaga caaagccgcg ggaggagcag  960
tacaacagca cgtaccgggt ggtcagcgtc ctcaccgtcc tgcaccagga ctggctgaat 1020
ggcaaggagt acaagtgcaa ggtctccaac aaagccctcc cagcccccat cgagaaaacc 1080
atctccaaag ccaaagggc agccccgaga accacaggtgt acaccctgcc cccatcccgg 1140
gatgagctga ccaagaacca ggtcagcctg acctgcctgg tcaaaggctt ctatcccagc 1200
gacatcgccg tggagtggga gagcaatggg cagccggaga acaactacaa gaccacgcct 1260
cccgtgctgg actccgacgg ctccttcttc ctctacagca agctcaccgt ggacaagagc 1320
aggtggcagc aggggaacgt cttctcatgc tccgtgatgc atgaggctct gcacaaccac 1380
tacacgcaga agagcctctc cctgtctccg ggtaaaggat cttccgaaac gcaggccaga 1440
tcgaccacag atgctctgaa cgttcttctc atcatcgtgg atgacctgcg ccctctcctg 1500
ggctgttatg gggataagct ggtgaggtcc ccaaatattg accaactggc atcccacagc 1560
ctcctcttcc agaatgcctt tgcgcagcaa gcagtgtgcg cccgagccg cgtttctttc 1620
ctcactggca ggagacctga caccaccgc ctgtacgact caactcctca ctggagggtg 1680
cacgctggaa acttctccac catcccccag tacttcaagg agaatggcta tgtgaccatg 1740
```

```
tcggtgggaa aagtctttca ccctgggata tcttctaacc ataccgatga ttctccgtat  1800
agctggtctt ttccaccta tcatccttcc tctgagaagt atgaaaacac taagacatgt  1860
cgagggccag atggagaact ccatgccaac ctgctttgcc ctgtggatgt gctggatgtt  1920
cccgagggca ccttgcctga caaacagagc actgagcaag ccatacagtt gttggaaaag  1980
atgaaaacgt cagccagtcc tttcttcctg gccgttggt atcataagcc acacatcccc  2040
ttcagatacc ccaaggaatt tcagaagttg tatcccttgg agaacatcac cctggccccc  2100
gatcccgagg tccctgatgg cctacccct gtggcctaca acccctggat ggacatcagg  2160
caacgggaag acgtccaagc cttaaacatc agtgtgccgt atggtccaat tcctgtggac  2220
tttcagcgga aaatccgcca gagctacttt gcctctgtgt catatttgga tacacaggtc  2280
ggccgcctct tgagtgcttt ggacgatctt cagctgccaa acagcaccat cattgcattt  2340
acctcggatc atgggtgggc tctaggtgaa catggagaat gggccaaata cagcaatttt  2400
gatgttgcta cccatgttcc cctgatattc tatgttcctg gaaggacggc ttcacttccg  2460
gaggcaggcg agaagctttt cccttacctc gacccttttg attccgcctc acagttgatg  2520
gagccaggca ggcaatccat ggaccttgtg gaacttgtgt ctcttttcc cacgctggct  2580
ggacttgcag gactgcaggt tccacctcgc tgcccgttc cttcatttca cgttgagctg  2640
tgcagagaag gcaagaacct tctgaagcat tttcgattcc gtgacttgga agaagatccg  2700
tacctccctg gtaatcccg tgaactgatt gcctatagcc agtatcccg gccttcagac  2760
atccctcagt ggaattctga caagccgagt ttaaaagata taaagatcat gggctattcc  2820
atacgcacca tagactatag gtatactgtg tgggttggct tcaatcctga tgaatttcta  2880
gctaactttt ctgacatcca tgcaggggaa ctgtattttg tggattctga cccattgcag  2940
gatcacaata tgtataatga ttcccaaggt ggagaccttt tccagttgtt gatgccttaa  3000
gcggccgc                                                            3008

SEQ ID NO: 8           moltype = AA   length = 975
FEATURE                Location/Qualifiers
REGION                 1..975
                       note = Amino acid sequence of fused protein of the
                       heavy-chainof humanized anti-hTfR antibody and hI2S
source                 1..975
                       mol_type = protein
                       organism = synthetic construct
SEQUENCE: 8
EVQLVQSGAE VKKPGESLKI SCKGSGYSFM NYWLGWVRQM PGKGLEWIGD IYPGGDYPTY   60
SEKFKVKAII SADTSISTVY LQLSSLKASD TAMYFCARSG NYDEVAYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPGKGS SETQANSTTD ALNVLLIIVD DLRPSLGCYG  480
DKLVRSPNID QLASHSLLFQ NAFAQQAVCA PSRVSFLTGR RPDTTRLYDF NSYWRVHAGN  540
FSTIPQYFKE NGYVTMSVGK VFHPGISSNH TDDSPYSWSF PPYHPSSEKY ENTKTCRGPD  600
GELHANLLCP VDVLDVPEGT LPDKQSTEQA IQLLEKMKTS ASPFFLAVGY HKPHIPFRYP  660
KEFQKLYPLE NITLAPDPEV PDGLPPVAYN PWMDIRQRED VQALNISVPY GPIPVDFQRK  720
IRQSYFASVS YLDTQVGRLL SALDDLQLAN STIIAFTSDH GWALGEHGEW AKYSNFDVAT  780
HVPLIFYVPG RTASLPEAGE KLFPYLDPFD SASQLMEPGR QSMDLVELVS LFPTLAGLAG  840
LQVPPRCPVP SFHVELCREG KNLLKHFRFR DLEEDPYLPG NPRELIAYSQ YPRPSDIPQW  900
NSDKPSLKDI KIMGYSIRTI DYRYTVWVGF NPDEFLANFS DIHAGELYFV DSDPLQDHNM  960
YNDSQGGDLF QLLMP                                                   975
```